US009394220B2

(12) United States Patent
Jemaa et al.

(10) Patent No.: US 9,394,220 B2
(45) Date of Patent: Jul. 19, 2016

(54) METHOD FOR PRODUCING BIO-METHANOL AT PULP MILLS

(71) Applicant: FPINNOVATIONS, Pointe-Claire (CA)

(72) Inventors: Naceur Jemaa, Pointe-Claire (CA); Michael Paleologou, Beaconsfield (CA)

(73) Assignee: FPINNOVATIONS, St-Jean, Pointe-Claire, Quebec H9R 3J9 (CA)

( * ) Notice: Subject to any disclaimer, the term of this patent is extended or adjusted under 35 U.S.C. 154(b) by 0 days.

(21) Appl. No.: 14/897,691

(22) PCT Filed: Jun. 16, 2014

(86) PCT No.: PCT/CA2014/050559
§ 371 (c)(1),
(2) Date: Dec. 11, 2015

(87) PCT Pub. No.: WO2014/201555
PCT Pub. Date: Dec. 24, 2014

(65) Prior Publication Data
US 2016/0122267 A1    May 5, 2016

Related U.S. Application Data

(60) Provisional application No. 61/836,962, filed on Jun. 19, 2013.

(51) Int. Cl.
| | |
|---|---|
| *C07C 29/76* | (2006.01) |
| *B01D 3/00* | (2006.01) |
| *C07C 29/80* | (2006.01) |
| *D21C 11/02* | (2006.01) |
| *B01D 3/14* | (2006.01) |
| *B01D 15/08* | (2006.01) |
| *B01D 61/02* | (2006.01) |

(52) U.S. Cl.
CPC ............... *C07C 29/76* (2013.01); *B01D 3/002* (2013.01); *B01D 3/145* (2013.01); *B01D 3/148* (2013.01); *B01D 15/08* (2013.01); *B01D 61/025* (2013.01); *C07C 29/80* (2013.01); *D21C 11/02* (2013.01); *B01D 2311/2626* (2013.01); *B01D 2311/2646* (2013.01); *B01D 2311/2669* (2013.01); *B01D 2311/2673* (2013.01)

(58) Field of Classification Search
CPC ........ C07C 29/76; C07C 29/80; B01D 3/002; B01D 3/145; B01D 3/148
USPC .................... 568/913; 210/259; 202/153, 155
See application file for complete search history.

(56) References Cited

U.S. PATENT DOCUMENTS

| | | | |
|---|---|---|---|
| 4,759,850 | A | 7/1988 | Farnand et al. |
| 5,063,250 | A | 11/1991 | Murayama et al. |
| 5,387,322 | A | 2/1995 | Cialkowski et al. |
| 5,863,391 | A | 1/1999 | Rueter et al. |
| 6,110,376 | A | 8/2000 | Savage et al. |
| 6,214,176 | B1 | 4/2001 | Sherman et al. |
| 7,138,536 | B2 | 11/2006 | Bournay et al. |
| 7,365,220 | B2 | 4/2008 | Lewis et al. |
| 8,349,130 | B2 | 1/2013 | Jemaa et al. |
| 2011/0306807 | A1 | 12/2011 | Der et al. |

FOREIGN PATENT DOCUMENTS

| | | |
|---|---|---|
| WO | 2012026373 | 3/2012 |
| WO | 2012156461 | 11/2012 |

OTHER PUBLICATIONS

Niemela, K., Sulfur and Nitrogen Compounds in Rectified Methanol from Foul Condensate Stripping, PAPTAC/TAPPI International Chemical Recovery Conference Proceedings, Charleston, South Carolina, Jun. 6-11, 2004.
Jensen, A., Ip, T. and Percy, J. Methanol Purification System, 2012 TAPPI PEERS Conference, Savannah, Oct. 14-18, 2012, p. 1245.
Herbert H. P. Fang and EdwardS. K. Chian "Reverse Osmosis Separation of Polar Organic Compounds in Aqueous Solution" Environnemental Science & Techno logie, vol. I 0 (4), pp. 364-369, 1976.
Janet Corson MacNeil <<Membrane Separation Technologies for Treatment of Hazardous Wastes CRC Critical Reviews in Environmental Control, vol. 18(2), pp. 91-131, 1988.
Jun Fang, et al. "Studies on Reverse Osmosis Separation of Aqueous Organic Solutions by P ANPSF Composite membrane" Chinese Journal of Polymer Science, vol. 18(2) pp. 115-122, 2000.
English language translation of WO2012/026373.
International Search Report from corresponding PCT/CA2014/050559.

*Primary Examiner* — Sikarl Witherspoon
(74) *Attorney, Agent, or Firm* — Norton Rose Fulbright Canada LLP

(57) ABSTRACT

The present invention describes a process and system of producing methanol from methanol condensates. In a preferred embodiment the condensates are biomethanol condensates from chemical pulp mills and various waste sources used to produce a purified biomethanol. Pulp condensates are rich in methanol and contain many other contaminants. Presently, most chemical pulp mills, such as Kraft pulp mills use steam stripping to remove and concentrate the methanol and burn the methanol onsite along with the contaminants. A combination of treatments that include air stripping, steam stripping, distillation and reverse osmosis is described to obtain purified biomethanol suitable for sale or use on site.

17 Claims, 6 Drawing Sheets

METHOD FOR PRODUCING BIO-METHANOL AT PULP MILLS

CROSS-REFERENCE TO RELATED APPLICATIONS

This application is a National entry of PCT/CA2014/050559 filed Jun. 16, 2014, in which the United States of America was designated and elected, and which remains pending in the International phase until Dec. 19, 2015, which application in turn claims priority under 35 USC 119(e) from U.S. Provisional Application Ser. No. 61/836,962, filed Jun. 19, 2013.

BACKGROUND OF THE INVENTION

1. Field of the Invention

The present invention describes a method and system to produce highly purified methanol from a methanol condensate wherein a preferred embodiment the methanol condensate is a biomethanol from biomass sources.

2. Description of the Prior Art

Chemical pulp mills, including Kraft mills generate considerable amounts of condensates during the pulp-making process. Condensates contain several undesirable compounds that make their recycle and reuse impossible without treatment. Condensates are generally generated in the black liquor evaporation and digester areas. Methanol condensates can also be obtained from other sources such as pulp and municipal wastes.

It has been reported that condensates generated at kraft pulp mills contain several volatile organic compounds (VOCs), total reduced sulphur (TRS) compounds, and traces of black liquor. More than 150 compounds have been detected in foul condensates from kraft pulp mills (Niemela, K., Sulfur and Nitrogen Compounds in Rectified Methanol from Foul Condensate Stripping, PAPTAC/TAPPI International Chemical Recovery Conference Proceedings, Charleston, S.C., Jun. 6-11, 2004). The main total reduced sulphur (TRS) compounds reported are hydrogen sulphide ($H_2S$), methyl mercaptan ($CH_3SH$), dimethyl sulphide ($CH_3SCH_3$), and dimethyl disulphide ($CH_3SSCH_3$). The TRS compounds have an offensive odour and their direct discharge to the ambient air or to an effluent treatment system can raise odour concerns from the communities near the mill and/or may cause the mill to exceed its emission limits with respect to these compounds. Other VOCs include methanol, ethanol, acetone, and terpenes. Methanol is by far the major VOC in kraft pulp mill condensates.

The major foul condensate treatment methods at kraft pulp mills include air and steam stripping. Air stripping removes only TRS compounds and requires an air to condensate ratio of 3-5% on a mass basis. The gaseous stream is then burned in a boiler, kiln, or an incinerator. The TRS removal efficiency is a function of temperature and pH of the feed solution. Generally, this approach removes more than 90% of the TRS compounds present in the condensate. Only a few mills in North America air strip their condensates.

Steam stripping is the dominant condensate treatment approach in the pulp and paper industry. To remove most of the TRS compounds and most of the methanol in the feed stream, a steam to condensate ratio of 15-20% on a mass basis is required. The TRS compounds, the turpentine (softwood pulp mills) and methanol are concentrated in the stripper-off gases (SOG). These gases are commonly burned in the recovery boiler, power boiler, lime kiln, or in a dedicated incinerator.

Most of the methanol on the market is produced from natural gas by steam reforming. During this process, natural gas is first converted into synthesis gas consisting of CO, $CO_2$, $H_2O$, and $H_2$. These gases are then catalytically converted to methanol. In fact, methanol can be produced from any resource that can be converted to synthesis gas such as biomass, agriculture residue, municipal and industrial wastes, and other feedstocks. These steps take place at high temperatures and pressures. The crude product containing methanol, water, and other high boilers is purified by distillation. Sodium hydroxide can be added to reduce carbon steel corrosion and avoid an expensive metallurgy. The sodium hydroxide reacts with organic acids present in the raw methanol and reduces their concentration levels in the methanol final products.

Several patents such as U.S. Pat. Nos. 5,063,250, 5,387,322, 6,214,176, describe the distillation of raw methanol obtained from methane steam reforming.

U.S. Pat. No. 5,863,391 describes a method to purify methanol by removing acetaldehyde using extractive distillation. Ethyl glycol was used in this case to enhance the volatility of acetaldehyde.

A significant amount of methanol can be present in the foul condensate at kraft pulp mills which ends up in the stripper-off gas. Few attempts have been made to recover or to further purify the methanol content of these streams for use within the mill or for sale for specific applications.

US Patent Application 2011/0306807 A1 described a method of producing methanol from SOG condensate. The SOG condensate is decanted to remove terpenes and then two distillation columns are employed to purify the methanol. FIG. 1 presents the layout of the process as implemented at a kraft pulp mill (Jensen, A., Ip, T. and Percy, J. Methanol Purification System, 2012 TAPPI PEERS Conference, Savannah, Oct. 14-18, 2012, page 1245). High purity methanol (99.85%) was the target of this process. However, the presence of several contaminants such as sulfur and nitrogen species made it difficult to reach a final methanol product that is suitable for sale and meets the International Methanol Producers and Consumers Association (IMPCA) standards. Further treatment of the condensate and/or the final product is required to achieve the desired methanol quality suitable for sale.

SUMMARY OF THE INVENTION

In accordance with one aspect of the present invention, there is provided a process for producing a biomethanol from a pretreated methanol condensate, the process comprising the step of treating the condensate by reverse osmosis to produce the biomethanol.

In accordance with one aspect of the process herein described, there is provided a process for producing a purified methanol comprising pretreating a methanol condensate to produce a pretreated condensate; polishing the pretreated condensate by reverse osmosis to produce the purified methanol.

In accordance with another aspect of the process herein described, the pretreating comprises removal of impurities from the methanol condensate to from 1 to 300 mg/L of total reduced sulphur (TRS); from 0 to 1000 mg/L total sulfur; from 0 to 100 mg/L terpenes; and from 0 to 500 mg/L acetone.

In accordance with another aspect of the process herein described, the polishing by reverse osmosis has an impurity removal efficiency of greater than 95% by weight.

In accordance with yet another aspect of the process herein described, the polishing by reverse osmosis has an impurity removal efficiency of greater than 97% by weight.

In accordance with yet another aspect of the process herein described, the methanol condensate is a biomethanol condensate that derives from a biological source.

In accordance with still another aspect of the process herein described, the pretreating the biomethanol comprises acidifying the biomethanol condensate; steam stripping VOCs from the acidified condensate to produce a SOG condensate; decanting the SOG condensate into a methanol rich stream; and distilling the methanol rich stream to produce the pretreated methanol.

In accordance with yet still another aspect of the process herein described, the pretreating includes an air stripping step after the acidifying the biomethanol.

In accordance with a further aspect of the process herein described, the process further comprising a second methanol polishing step with activated carbon of the purified methanol from reverse osmosis to produce an IMPCA biomethanol having a composition of: at least 99.85% methanol by weight on a dry basis; at most 30 mg/kg acetone, and at most 0.5 mg/kg sulphur.

In accordance with still another aspect of the invention, there is provided a system for producing a purified methanol from a pretreated methanol condensate comprising contaminants, the system comprising the improvement of: a reverse osmosis unit polishing the methanol condensate to produce the purified methanol.

In accordance with yet a further aspect of the system herein described, the methanol condensate is a biomethanol condensate that derives from a biological source.

In accordance with yet still another aspect of the system herein described, there is provided a system further comprising an activated carbon unit downstream of the reverse osmosis unit producing an IMPCA methanol having a composition of: at least 99.85% methanol by weight on a dry basis; at most 30 mg/kg acetone, and at most 0.5 mg/kg sulphur.

In accordance with yet still another aspect of the present invention, there is provided a system for producing a purified methanol from a methanol condensate comprising contaminants and turpentine, the system comprising: a steam stripper producing a stripper off gas; a condenser condensing the stripper off gas to a VOC free condensate; a decanter separating the VOC free condensate into a turpentine stream and a methanol rich stream; a distillation system converting the methanol rich stream to a pretreated methanol; a reverse osmosis unit converting the pretreated methanol to the purified methanol.

In accordance with yet still another aspect of the system herein described, further comprising an activated carbon unit converting the methanol to an IMPCA biomethanol having a composition of: at least 99.85% methanol by weight on a dry basis; at most 30 mg/kg acetone, and at most 0.5 mg/kg sulphur, the methanol condensate is a biomethanol condensate.

In accordance with yet still another aspect of the system herein described, further comprising an air stripper upstream of the steam stripper.

In accordance with yet still another aspect of the system herein described, the distillation system comprises two distillation columns and a surge tank between the two columns for removing contaminants from the methanol rich stream.

It is an object of this invention to provide a method of treating pulp mill waste condensate streams containing methanol, to produce a biomethanol with high purity that meets the IMPCA standards and is suitable for sale and suitable for internal use at the pulp mill in the chlorine dioxide generator.

It is a particular object of this invention to provide a method of removing odorous and other undesirable compounds from a methanol-water solution.

It is a further object of this invention to provide a method of recovering some of the sulfur species from condensate for use in the flavoring industry.

It is still a further object of this invention to provide a method of recovering sulphur-free turpentine.

In accordance with one aspect of the invention, there is provided a method for recovering and purifying methanol from an aqueous kraft pulp mill condensate stream comprising:

Flowing the foul condensate through a steam stripper, condensing the stripper off gas condensate, separating the methanol-rich phase from the terpene phase, removing the volatile compounds by heating the stream in a distillation column, adding an oxidant or a precipitation agent to reduce the sulfur content, passing the methanol stream through a second distillation unit to separate methanol from other higher boilers, employing reverse osmosis to remove high molecular weight compounds, and using activated carbon to polish the final methanol product to meet the IMPCA standards.

In one aspect of the invention there is provided a process for recovering methanol from foul condensate from pulp mills comprising:

Flowing the foul condensate through an air stripping unit to remove TRS compounds, condensing the stripper off gas condensate, separating the methanol-rich phase from the terpene phase, removing the volatile compounds by heating the stream in a distillation column, adding an oxidant or a precipitation agent to reduce the sulfur content, passing the methanol stream through a second distillation unit to separate methanol from other higher boilers, employing reverse osmosis to remove high molecular weight compounds, and using activated carbon to polish the final methanol product to meet the IMPCA standards.

DETAILED DESCRIPTION OF THE INVENTION

Figure 1:
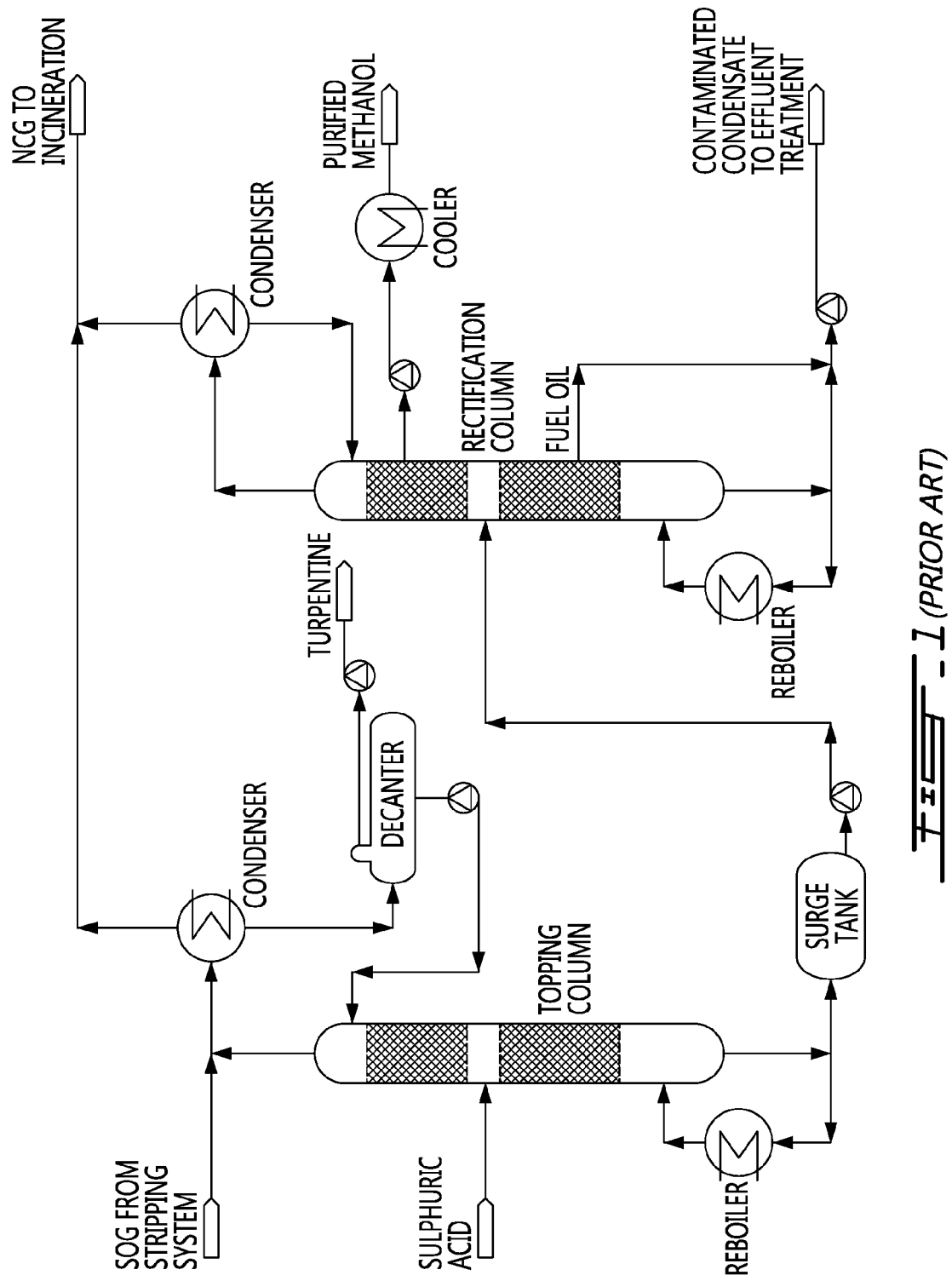
FIG. 1 is a schematic diagram of the Lundberg methanol purification process at a pulp mill (PRIOR ART)

The objective of this work was to devise a cost-effective approach to purify the foul condensate at kraft pulp mills and to recover clean methanol for use on site (i.e., in the chlorine dioxide generator as a reducing agent) and/or for sale. The recovered methanol had to be free of sulfur and nitrogen compounds. Pure bio-methanol for sale that meets the International Methanol Producers & Consumers Association (IMPAC) specification is possible to produce using the proposed approach.

It is described that methanol, and in a preferred embodiment, biomethanol can be polished in a liquid phase by reverse osmosis. Contaminant removal efficiencies are above 95% by weight, and the polished methanol produced from RO reduced the size of the carbon adsorption unit required to obtain methanol with IMPAC specifications.

DEFINITIONS

Polishing is defined as a process that removes a small amount of residual contaminants from a process stream, in this case, polishing is used to define the removal of residue contaminants from a pretreated methanol condensate stream by reverse osmosis and/or by activated carbon.

Removal efficiency is defined as $RE=(W_{in}-W_{out})/W_{in} \times 100$, Where $W_{in}$=mass of a particular contaminant before a process, $W_{in}$=mass of the contaminant after the process.

Free of VOCs is defined as substantially free of volatile organic compounds, where substantially is understood as virtually undetectable.

Biomethanol is defined as a methanol produced from a renewable resource.

Many types of methanol condensates can be envisaged that are applicable to treatment by the process and system described herein such as the ones from chemical pulp mills or their wastes, which are rich in methanol, TRS compounds and terpenes (in the case of softwood pulp mills). In addition, it has been reported that these condensates contain over 150 chemical species. The separation of methanol from all of these contaminants is not a straightforward task. Presently, no approach has been devised and implemented to produce methanol that meets the IMPCA standards from pulp mill streams. Methanol condensates from other waste sources such as household wastes, are also compatible with this methanol purification system, that include a large number of by-products.

The methanol or foul condensate from pulp mills is generally treated in a steam stripper to remove the methanol, the terpenes, and several other volatile species such as TRS compounds, acetone, ethanol, acetic acid, and various sulfur/nitrogen-containing chemical compounds. This stream called stripper off gases is usually burned in the recovery boiler, power boiler, lime kiln, or in a dedicated incinerator. As described in US Patent application 2011/0306807 and illustrated in FIG. 1, to recover methanol, the SOG can be first condensed and then the terpenes are separated from the methanol-rich phase in a decanter. The methanol-rich phase can be sent to a set of distillation columns for further purification. In the first column, TRS compounds are removed. We found that the removal of sulfur compounds can be enhanced through the addition of oxidants (i.e., hypochlorite) or precipitation agents (i.e., ferric sulfate, calcium oxide) after the first column. In a second column, the methanol can be concentrated and collected from the top of the column while other contaminants are released from the bottom and the middle of the column. The methanol thus obtained may still contain significant amounts of impurities such as sulfur and nitrogen compounds.

To remove these contaminants the inventor surprisingly found that a reverse osmosis unit can be employed to polish the contaminants from the methanol. The concentrate from the RO system can be recycled back to the methanol plant while the permeate can be further treated with activated carbon to remove any traces of TRS and other organic compounds. Theoretically, only methanol and traces of water should pass through the RO membrane. The concentrate from the RO system can be further treated to recover other valuable chemicals such as 3,5-Dimethyl-1,2,4-trithiolane ($C_4H_8S_3$) used in the flavoring industry.

In another configuration, the foul condensate can be passed first through an air stripper to remove the TRS compounds. Several mass transfer devices can be used for this purpose such as, but not limited to, a packed column or a hollow fiber contactor. Chemical oxidants such as but not limited to hydrogen peroxide, hypochlorite, chlorine dioxide, and oxone can be added to destroy any remaining sulfur compounds in the stripped condensate. Prior to air stripping, the foul condensate is preferably acidified. The acidification is performed by the addition of any inorganic or organic acid but preferably with sulfuric acid. The acidification lowers the pH of the condensate thus avoiding the release of nitrogen compounds during the subsequent steam stripping step. The treated condensate is then passed through a steam stripper. The SOG from the steam stripper should contain mainly methanol and terpenes which can be separated using a decanter. A distillation column is used to concentrate and purify further the methanol to the desired level. RO can be used to remove the majority of contaminants from the methanol while activated carbon can be used as a polishing step to purify further the methanol.

Foul condensate from kraft pulp mills contains methanol, turpentine, other volatile compounds and several sulfur and nitrogen compounds. The methanol concentration in foul condensate can range from less than 1 g/L to about 30 g/L depending on the wood type used (softwood or hardwood) and the pulping conditions.

Furthermore, sulfite (ammonium, magnesium, calcium or sodium base) pulp mills produce acidic condensate which contains $SO_2$, methanol and other chemicals. To this type of condensate ammonium hydroxide (or magnesium hydroxide or sodium hydroxide or calcium hydroxide) can be added to bind the $SO_2$. Ammonium sulfite (magnesium sulfite or sodium sulfite) can be separated by using RO while methanol will pass through the membrane. The ammonium sulfite (magnesium sulfite or sodium sulfite) obtained in the membrane concentrate can be recycled to the cooking plant. The permeate or RO treated condensate can be further concentrated and purified using any combination of steam stripping, distillation, RO, and activated carbon to produce bio-methanol that meets the IMPAC specifications.

Figure 2:
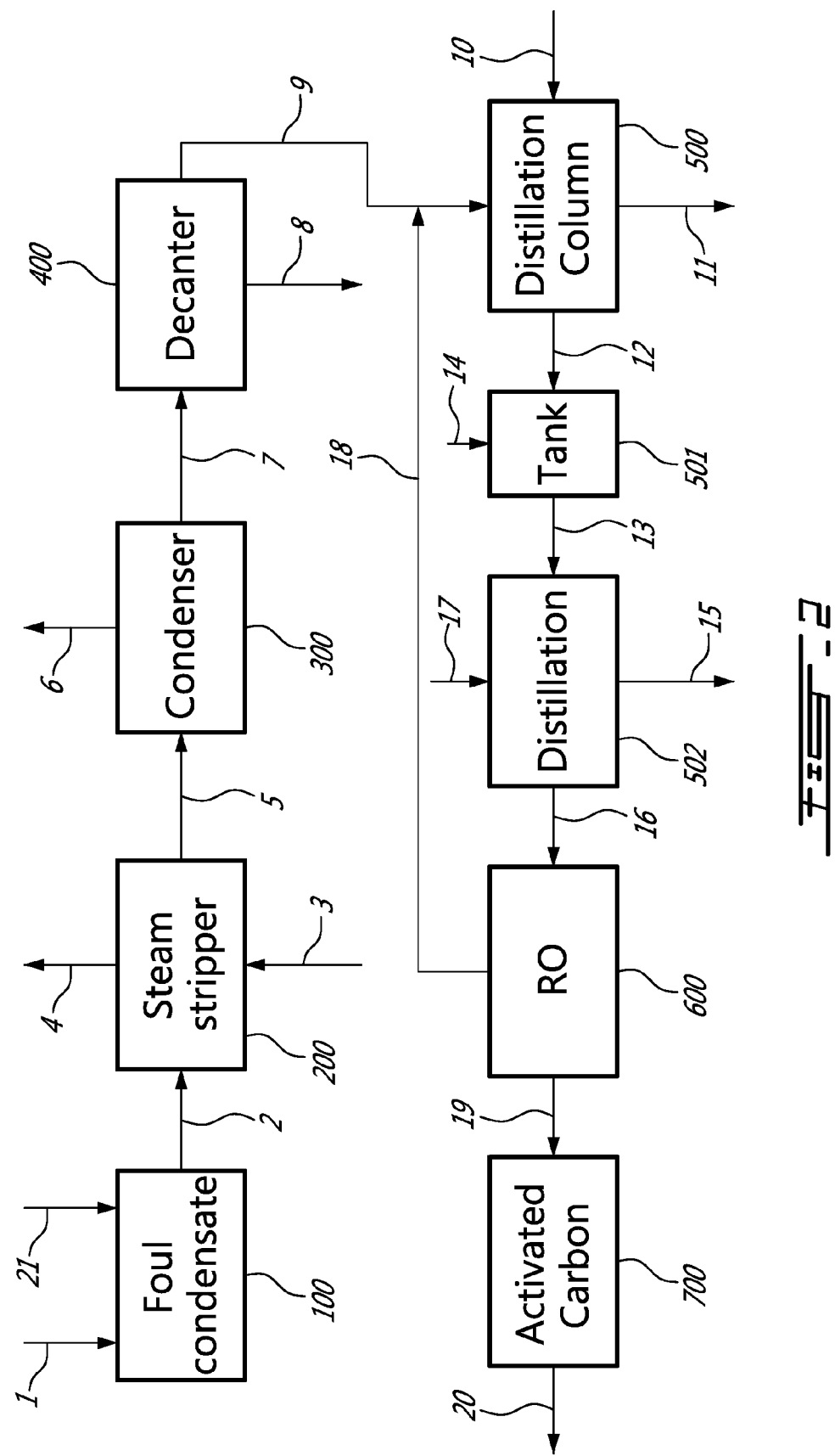
FIG. 2 is a process flow diagram of the production of a high purity biomethanol from a foul condensate of a pulp mill according to one embodiment of the present invention.

In the preferred embodiment shown in FIG. 2, foul condensate, 1 is fed to a receiving tank, 100. An acid such as sulfuric acid 21 can be added to lower the pH of the condensate. The condensate is rich in ammonia and ammonium compounds. By lowering the pH of the condensate, the ammonia and ammonium compounds will be converted to ammonium sulphate which is not volatile. The acidic condensate 2 is then fed to a steam stripper 200. The steam stripper uses steam 3 to strip and remove volatile compounds such as totally reduced sulfur compounds, methanol, terpenes, and other volatile organic compounds. The treated condensate 4 is recycled within the pulp mill for other uses. The stripper off gases 5 from the steam stripper are condensed in a condenser 300. The off gases 6 are burnt in the pulp mill lime kiln, or a boiler, or a dedicated incinerator. The stripper off gas condensate 7 is sent to a decanter 400 to separate the mixture into a methanol-rich stream 9 and a turpentine stream 8. The methanol-rich stream 9 contains 15% to 80% methanol by weight. This stream 9 is sent to a distillation plant 500. The distillation plant can have two columns operating in series. Steam 10 is fed to the first distillation column 500 which removes total reduced sulfur compounds, non-condensables and compounds with low boiling point, stream 11. The methanol-rich stream 12 exits the bottom of the first column and is fed to a tank 501. The removal of sulfur compounds can be enhanced through the addition of oxidants (i.e., hypochlorite) or precipitation agents, stream 14, (i.e., ferric sulfate, calcium oxide). A precipitate 25 can be removed from the bottom of tank 501. The treated stream 13 is fed to a second distillation column 502. Steam 17 is fed to the second distillation column 502. The high boilers 15 are removed from the bottom of the column. From the distillation plant, a methanol-rich stream 16 is obtained. However, this methanol stream does not meet the IMPCA specifications and can still contain several sulfur and nitrogen compounds, acetone, and other impurities. To purify it further, a reverse osmosis unit 600 can be used. The methanol-rich stream 16 from the distillation system is understood to be the pretreated kraft pulp foul condensate, that can be treated in the RO unit 600. An RO membrane is ideally supposed to retain all chemical species other than water and methanol. Several types of RO membranes such as tubular or spiral wound membranes are available and can be used. Polymeric membranes made of polysulphone, polyethylene, or inorganic membranes can be used. The reject from the RO unit 18 is recycled to the distillation plant or used to recover flavoring compounds. Solid sodium hydroxide can be added to the RO feed (stream 16) to keep some of the volatiles such as $H_2S$ and mercaptan in the ionic non-volatile form. Alternatively, sodium hydroxide can be added to tank 501. The permeate 19 from the RO unit is understood as the biomethanol product that can be used in the plant (i.e., chlorine dioxide generator), but also can be fed to an activated carbon column 700 to remove any other traces of impurities and to obtain a biomethanol stream 20 that meets the IMPCA specifications. IMPCA Standard methanol is at least 99.85% weight methanol on a dry basis; max 50 mg/kg ethanol; max 0.5 mg/kg sulphur, max 30 mg/kg acetone; and max 1000 mg/kg (0.1% w/w) water. The density of pure methanol is about 792 g/L at room temperature. An RO unit can be used to purify stream 9 and make it suitable for use in the chlorine dioxide generator as a reducing agent or for other purposes (i.e., windshield fluid).

Figure 3:
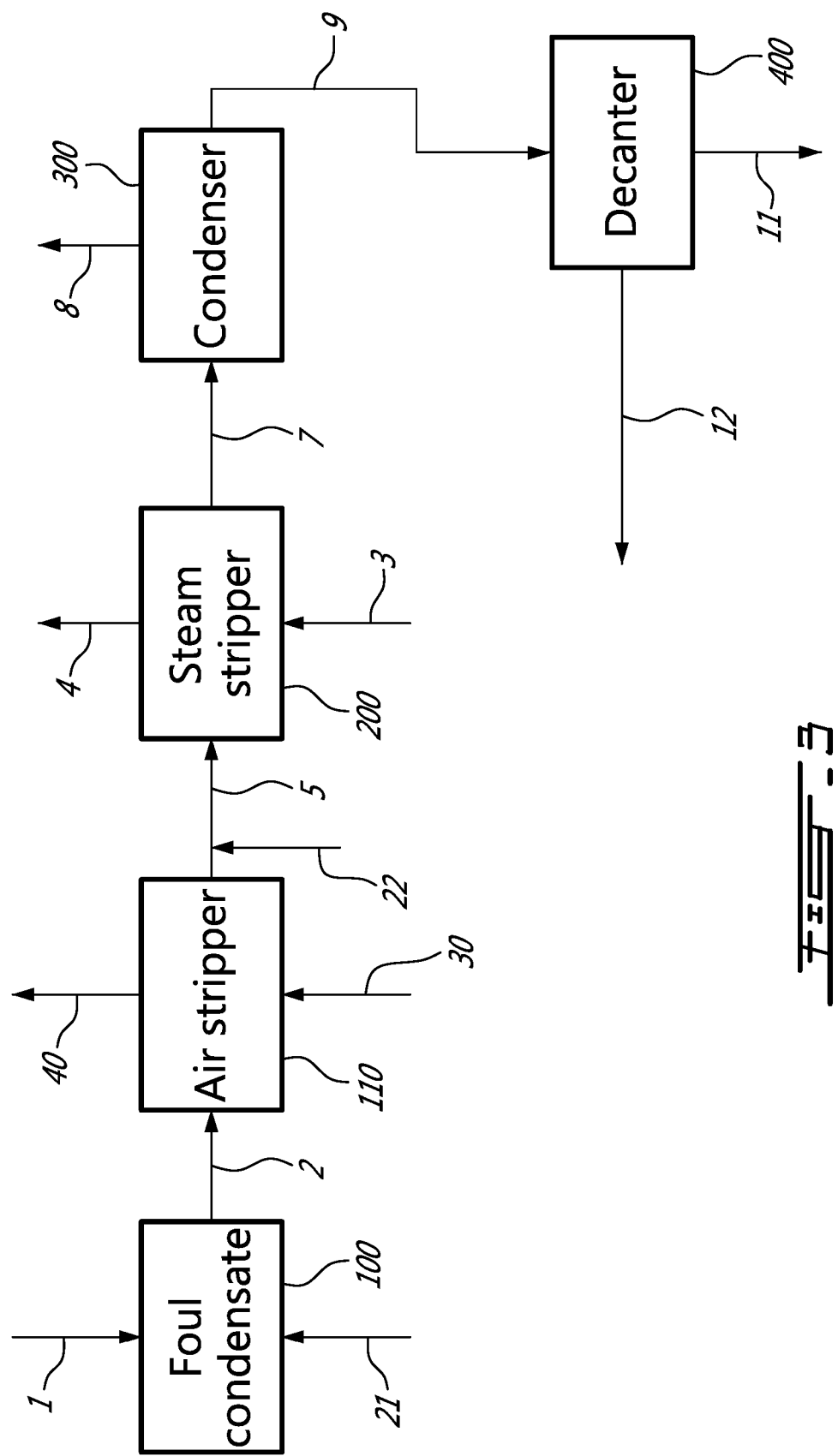
FIG. 3 is a process flow diagram of the production of a biomethanol/water mixture from a foul condensate of a pulp mill according to another embodiment of the present invention.

FIG. 3 presents a second configuration of the invention. Foul condensate 1 is fed to the foul condensate tank 100 where an acid such as sulfuric acid is added 21. The acidified condensate 2 is fed to a stripping unit 110. Air 30 is used to remove volatile compounds such as total reduced sulfur compounds. The air stripper 110 can be a tray or packed column or a multistage bubble air stripper. The condensate is preferably fed from the top while air is fed from the bottom. It can also be a series of hollow fiber contactors which are more efficient mass transfer devices. During these treatments, most of the methanol is expected to remain in the condensate. The contaminated air stream 40 can be burnt in the pulp mill lime kiln, a boiler, or a dedicated incinerator. The treated condensate 5 may still contain traces of TRS compounds. Oxidants 22 such as hydrogen peroxide, chlorine dioxide, hypochlorite, oxone, and peracetic acid can be added to destroy most of the remaining TRS compounds. The condensate is then fed to a steam stripper 200 where steam 3 is used to strip the methanol. The treated condensate 4 is recycled to the pulp mill for use in pulp washing and/or other purposes (i.e., lime mud and washing). The stripper off gases 7 are condensed in a condenser 300. The stripper off gases will thus be composed mainly of turpenes and methanol. Any non-condensable gases 8 are separated and burnt with stream 40. This aqueous mixture 9 is fed to a decanter 400. The sulfur-free terpenes 11 and the methanol stream 12 are separated from the decanter. The methanol obtained in this embodiment should contain 15% to 90% biomethanol. It may also contain other impurities such ethanol and acetone. This stream should be suitable for use as a reducing agent in the chlorine dioxide generator of chemical pulp mills as well as for other applications such as windshield washer fluid where a highly purified methanol is not required. The system may or may not require a reverse osmosis unit to attain the desired levels of contaminants.

Figure 4:
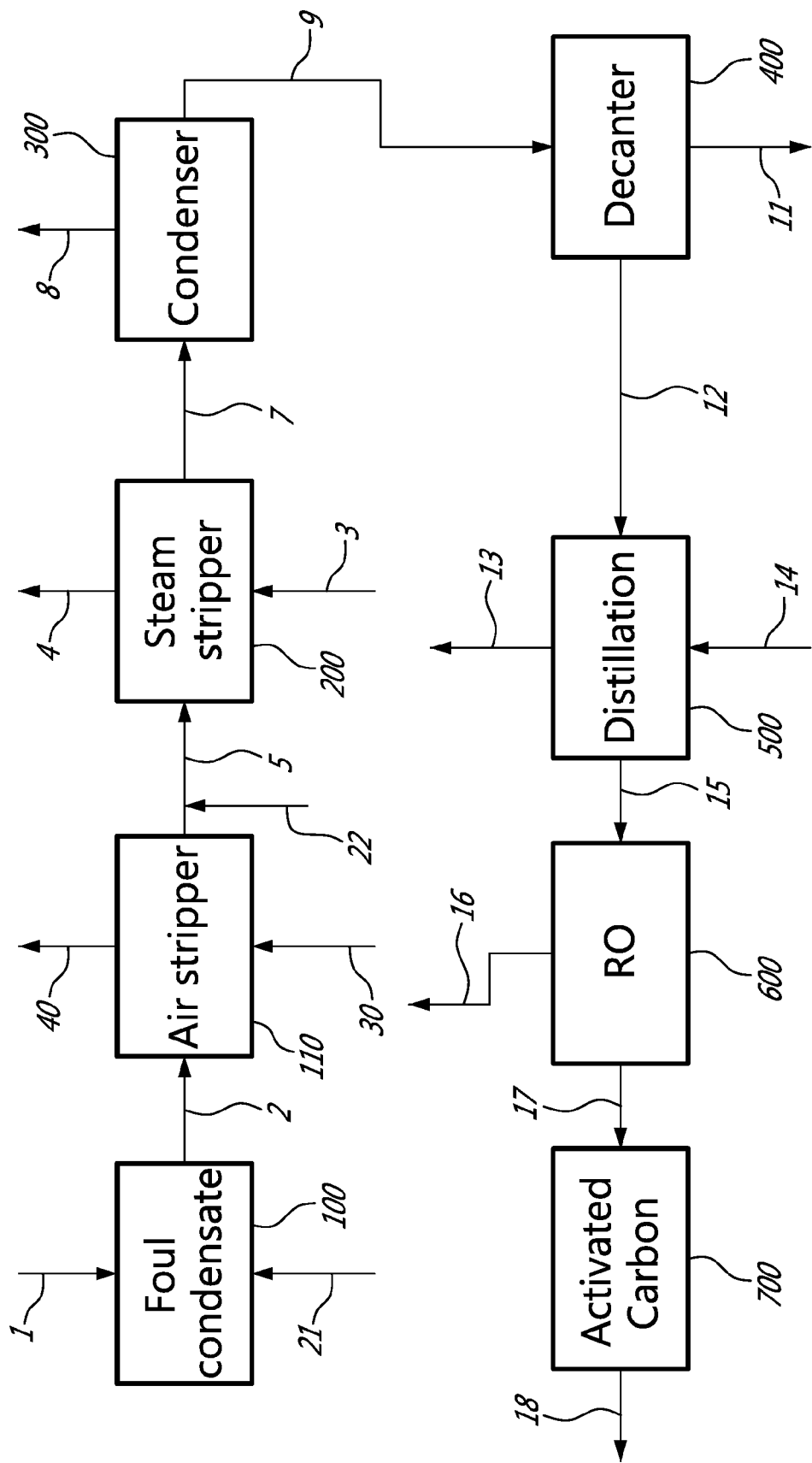
FIG. 4 is a process flow diagram of the production of a high purity biomethanol from a foul condensate of a pulp mill according to another embodiment of the present invention.

FIG. 4 uses a similar layout as that shown in FIG. 3 but the water-biomethanol mixture is further purified to obtain a highly purified biomethanol that meets the IMPCA standards. The water methanol mixture 12 from the decanter is fed to a distillation column 500. By applying steam 14 biomethanol is separated from the mixture. The other high boilers exit in stream 13. The biomethanol 15 which may contain traces of sulfur compounds such as 3,5-Dimethyl-1,2,4-trithiolane ($C_4H_8S_3$) is fed to an RO unit 600. We found that sulfur compounds such as 3,5-Dimethyl-1,2,4-trithiolane ($C_4H_8S_3$) are retained by the membrane and exit in stream 16. This stream can be further processed (i.e, evaporation to remove methanol) to recover this flavoring agent that has a high boiling point (228° C.). The membrane types and configuration mentioned in the description of FIG. 2 can be employed in this case. Further purification, if needed, can be accomplished by feeding the biomethanol stream from RO 17 to an activated carbon unit 700. The biomethanol final product 18 should meet the IMPCA specifications and should be suitable for sale.

Several sulfur and nitrogen compounds have been detected in the purified methanol product obtained after distilling the SOG condensate (FIG. 1). These compounds include:
3,5-Dimethyl-1,2,4-trithiolane: $C_4H_8S_3$
1,1-bis(methylthio)ethane: $C_4H_{10}S_2$
2-Thioxo-4-thiazolidinecarboxylic acid: $C_4H_5NO_2S_2$
1,2-Propanedithiol: $C_3H_8S_2$
1-[N-Aziridyl]propane-2-thiol: $C_5H_{11}NS$
disulfide, bis[1-(methylthio)ethyl]: $C_8H_{14}S_4$ 3,5-Dimethyl-1,2,4-trithiolane ($C_4H_8S_3$) is by far the sulfur compound most found in the methanol product after distillation. Its concentration ranges from 0 to 100 ppm in the samples analyzed. The recovery of 3,5-Dimethyl-1,2,4-trithiolane ($C_4H_8S_3$) from the concentrate of RO is effected by the present process. 3,5-Dimethyl-1,2,4-trithiolane ($C_4H_8S_3$) has been identified in the volatile flavor compounds of boiled beef (Chang et al in Chemistry and Industry, Nov. 23, 1968, pages 1639-1641) and is used as a food additive. The recovery of other compounds listed above is also possible in the process of the present invention.

Example 1

The bio-methanol obtained from a pulp mill after distillation of the SOG condensate (purified methanol of FIG. 1)

contains several sulfur compounds such as hydrogen sulphide, methyl mercaptan, dimethyl mercaptan, and dimethyl sulphide. Table I presents the concentration of TRS compounds of this stream. The total TRS is 152.2 ppm. To this stream, solid sodium hydroxide was added to insure that hydrogen sulphide and methyl mercaptan will be converted to the ionic form.

TABLE I

TRS in the biomethanol after distillation

| Compound | mg/L |
| --- | --- |
| Hydrogen Sulphide | 75.2 |
| Methyl Mercaptan | 6.9 |
| Dimethyl Sulphide | 0.0 |
| Dimethyl Disulphide | 99.7 |
| Total TRS (expressed as $H_2S$ equivalent) | 152.2 |

The biomethanol stream was passed through an RO membrane unit at 25° C. The RO membrane used was the TFC-HR membrane from Koch Membrane Systems, having a NaCl retention of 99.65%. The membrane had a surface area of about 28 cm$^2$. A constant pressure of about 200-400 psig was applied. The filtrate exiting the cell was collected in a separate container. The concentrate was circulated in the concentrate compartment of the filtration unit. After treatment, the total TRS was reduced to 4.8 ppm as indicated in Table II. The removal efficiency of the reverse osmosis unit was greater than 96% w/w. The total nitrogen content of the biomethanol was reduced from 500 ppm to 90 ppm after the RO treatment. The acetone content of the biomethanol stream was reduced by 90% after treatment with RO. Levels below the IMPCA specification (of less than 30 ppm) were achieved.

TABLE II

TRS in the biomethanol after RO treatment

| Compound | mg/L |
| --- | --- |
| Hydrogen Sulphide | 2.8 |
| Methyl Mercaptan | 0.6 |
| Dimethyl Sulphide | 0.0 |
| Dimethyl Disulphide | 2.1 |
| Total TRS expressed as $H_2S$ equivalent | 4.8 |

Figure 5A:
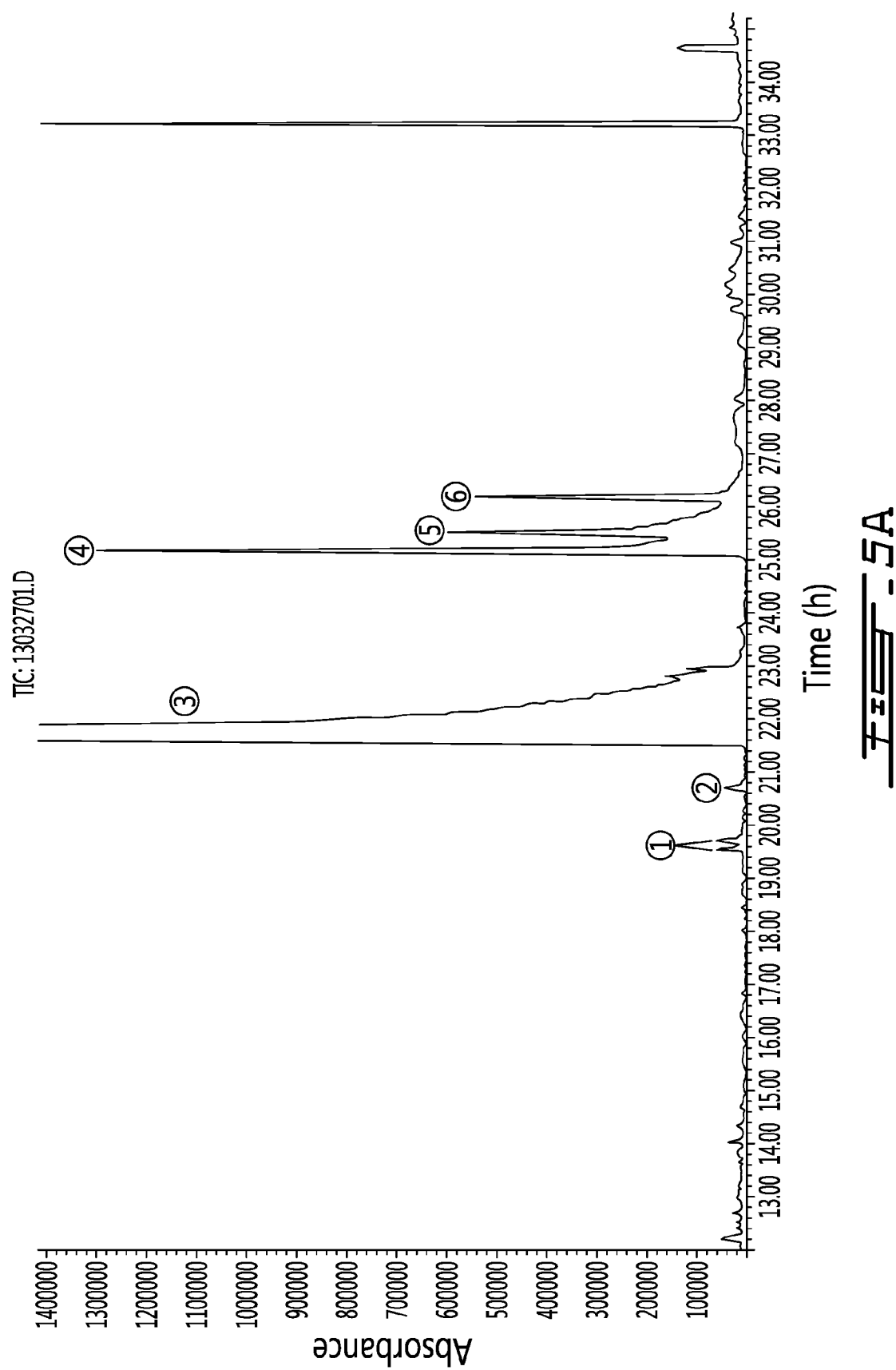
FIG. 5A is a gas chromatogram of a pretreated methanol condensate from a foul condensate feed of a pulp mill to a reverse osmosis unit used according to one embodiment of the present invention, including 6 main peaks: 1,2,4-Trithiolane, 3,5 dimethyl ($C_4H_8S_3$); 2) Ethane, 1,1-bis(methylthio)-($C_4H_{10}S_2$); 3) 1,2,5-thiadiazolidine,2,5-di-tert-butyl-,1,1-dioxide ($C_{10}H_{22}N_2O_2S$); 4) 2-Propen-1-amine, N-ethyl ($C_5H_{11}N$); 5) Thiazolidine, 2-methyl-($C_4H_9NS$); and 6) 1,3-Propanediamine,N,N,N',N'-tetramethyl-($C_7H_{18}N_2$) and a standard (hexamethylbenzene) shown on the far right of the figure.
Figure 5B:
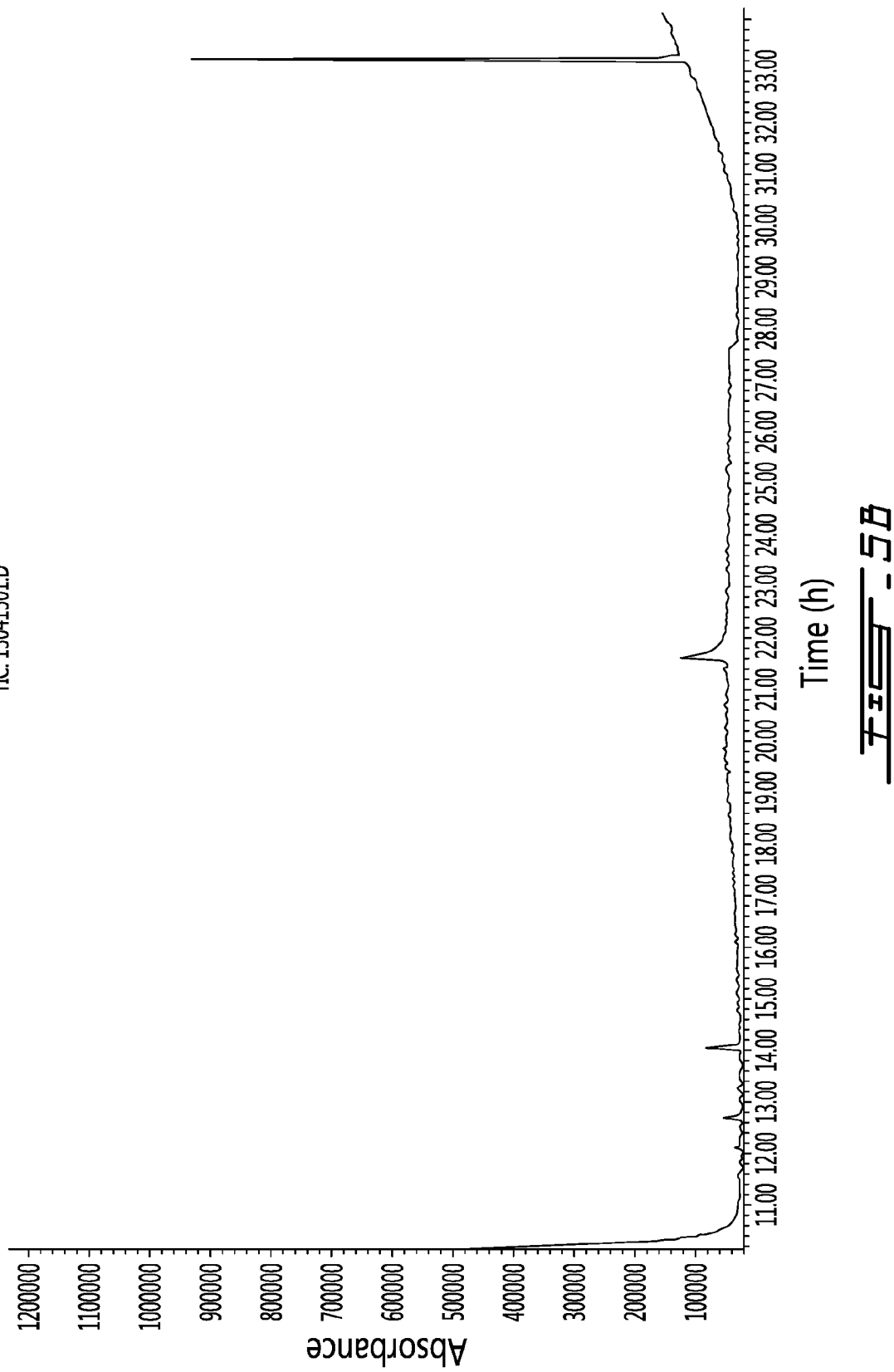
FIG. 5B is a gas chromatogram of a purified biomethanol from FIG. 5A after treatment by a reverse osmosis unit according to one embodiment of the present invention, where the 6 main peaks of FIG. 5A have substantially disappeared but with the standard (hexamethylbenzene) shown on the far right of the FIG. 5B.

In addition, the RO treatment removed other sulfur and nitrogen compounds. FIGS. 5A and 5B show chromatograms of two methanol samples injected into a GC system with a sulfur-specific detector before and after the RO treatment, respectively. Before treatment (FIG. 5A) compounds such as 3,5-Dimethyl-1,2,4-trithiolane: $C_4H_8S_3$ are clearly detected (Peak 1). The other peaks correspond to other sulfur and nitrogen compounds. The concentration of 3,5-Dimethyl-1,2,4-trithiolane: ($C_4H_8S_3$) in this particular sample is about 25 ppm. Hexane was used to extract these contaminants from the original methanol solution. Other sulfur and nitrogen containing compounds other than those shown in this figure have been detected in other samples. After RO (FIG. 5 B), no peaks in the chromatogram have been detected. These sulfur and nitrogen compounds were concentrated in the RO retentate. The RO unit does not concentrate the methanol feed considerably, it simply removes the remaining impurities in the condensate. Thus, to attain the IMPCA methanol standard, the methanol must be at a very high concentration (close to 99.85 wt % on a dry basis) to attain the level required by the IMPCA standard. If the concentration of the impurities is high, two or more RO units in series may be required to reduce impurity concentrations below the levels required for the IMPCA methanol standard.

The RO treated methanol was, subsequently, passed through an activated carbon unit to remove the remaining impurities. Table III shows the composition of the biomethanol after this treatment. Only about 0.1 mg/L TRS was left in the final product. These TRS compounds are more difficult to remove with RO compared to other sulfur-containing compounds such as 3,5-Dimethyl-1,2,4-trithiolane. The total sulfur content in the activated carbon-treated methanol sample was 3.2 ppm. The IMPCA sulfur requirement is 0.5 mg/kg or less. In addition, the activated carbon removes traces of acetone and ethanol. Furthermore, activated carbon reduced the total nitrogen content to less than 50 ppm.

TABLE III

TRS in the biomethanol after activated carbon treatment

| Compound | mg/L |
| --- | --- |
| Hydrogen Sulphide | 0.0 |
| Methyl Mercaptan | 0.0 |
| Dimethyl Sulphide | 0.0 |
| Dimethyl Disulphide | 0.2 |
| Total TRS | 0.1 |

Example 2

As mentioned above, treatment of the bio-methanol produced from a pulp mill after distillation of the SOG (FIG. 1) with several passes through an RO membrane can lower the contaminant levels to meet the IMPCA specifications. Table IV shows data after passing the methanol solution from a distillation plant five times through an RO unit. The sulfur dropped to 0.24 ppm while the acetone was 0 ppm. The initial sulfur content in the raw bio-methanol was 452 ppm. The bio-methanol purity was 99.98% after RO treatment. No activated carbon treatment is needed in this case.

TABLE IV

Bio-methanol treatment using RO

| | Permeate of the 5th pass |
| --- | --- |
| Sulfur, ppm | 0.24 |
| Acetone, ppm | 0 |
| Purity, % | 99.98 |

Example 3

Foul condensate from a sulfite pulp mill was obtained. It initially contained 619.3 ppm sulfur dioxide (as $SO_3^{2-}$). Concentrated ammonium hydroxide was added to convert the $SO_2$ to ammonium sulfite. The solution was passed through an RO system. About 96.7% of the ammonium sulfite was retained in the concentrate. The permeate contained only about 20.3 ppm of $SO_3^{2-}$ which can be further concentrated and purified to produce bio-methanol. The concentrate can be used in the acid cooking plant of an ammonium base sulfite pulp mill.

Example 4

As mentioned above, one way to reduce the sulfur and nitrogen content in the final methanol is to treat the rectification column feed. The rectification column feed is similar to the SOG condensate and is mostly water (about 70%). A rectification column feed solution has been treated with an RO membrane system. The permeate was analyzed and results are presented in Table V. The sulfur removal was about 94% while the nitrogen removal efficiency was about 85%. The removal of the sulfur and nitrogen compounds at this stage allows the rectification column to handle much less sulfur and nitrogen compounds. The final methanol product is expected to be much cleaner. Similarly, the SOG condensate can be purified with RO and employed in the chlorine dioxide generator or in other uses.

TABLE V

Treatment of a methanol-rich solution with RO

|  | Before RO | After RO |
| --- | --- | --- |
| Sulfur, ppm | 1358 | 77.7 |
| Nitrogen, ppm | 646 | 92.9 |

The invention claimed is:

1. A process for producing a purified methanol comprising:
   pretreating a methanol-containing condensate to produce a pretreated condensate;
   polishing the pretreated condensate by reverse osmosis to produce the purified methanol, and
   further polishing the polished methanol in a second polishing step to produce the purified methanol with activated carbon.

2. The process of claim 1, wherein the pretreating comprises removal of impurities from the methanol-containing condensate to
   from 1 to 300 mg/L of total reduced sulphur (TRS);
   from 0 to 1000 mg/L total sulfur;
   from 0 to 100 mg/L terpenes; and
   from 0 to 500 mg/L acetone.

3. The process of claim 1, wherein the polishing by reverse osmosis has an impurity removal efficiency of greater than 95% by weight.

4. The process of claim 1, wherein the polishing by reverse osmosis has an impurity removal efficiency of greater than 97% by weight.

5. The process of claim 1, wherein the methanol-containing condensate is a biomethanol containing condensate that derives from a biological source.

6. The process of claim 5, wherein the pretreating the biomethanol containing comprises acidifying the biomethanol condensate;
   steam stripping VOCs from the acidified condensate to produce a SOG condensate;
   decanting the SOG condensate into a methanol rich stream; and
   distilling the methanol rich stream to produce the pretreated methanol.

7. The process of claim 6, wherein pretreating includes an air stripping step after the acidifying the biomethanol.

8. The process of claim 1, wherein
   the second methanol polishing step produces an IMPCA-grade biomethanol having a composition of:
   at least 99.85% methanol by weight on a dry basis;
   at most 30 mg/kg acetone, and
   at most 0.5 mg/kg sulphur.

9. A system for producing a purified methanol from a pretreated methanol condensate comprising contaminants, the system comprising the improvement of:
   a reverse osmosis unit polishing the methanol condensate to produce the purified methanol, and
   an activated carbon unit.

10. The system of claim 9 wherein the methanol condensate is a biomethanol condensate that derives from a biological source.

11. The system of claim 9, the system further comprising an activated carbon unit downstream of the reverse osmosis unit producing the IMPCA grade methanol having a composition of:
    at least 99.85% methanol by weight on a dry basis;
    at most 30 mg/kg acetone, and at most 0.5 mg/kg sulphur.

12. A system for producing a purified methanol from a methanol containing condensate comprising contaminants and turpentine, the system comprising:
    a steam stripper producing a stripper off gas;
    a condenser condensing the stripper off gas;
    a decanter separating the SOG condensate into a turpentine stream and a methanol rich stream;
    a distillation system converting the methanol rich stream to a pretreated methanol;
    a reverse osmosis unit converting the pretreated methanol to the purified methanol, and
    an activated carbon until, converting the methanol to the purified methanol.

13. The system of claim 12, further comprising an air stripper upstream of the steam stripper.

14. The system of claim 12, wherein the activated carbon unit converting the methanol to an IMPCA grade biomethanol having a composition of:
    at least 99.85% methanol by weight on a dry basis;
    most 30 mg/kg acetone, and
    at most 0.5 mg/kg sulphur.

15. The system of claim 12, further comprising an air stripper upstream of the steam stripper.

16. The system of claim 12, wherein the distillation system comprises two distillation columns and a surge tank between the two columns for removing contaminants from the methanol rich stream.

17. The process of claim 7, wherein oxidants or precipitation agents are added to the pretreated methanol to precipitate sulfur compounds before further distilling the sulfur precipitated methanol.

* * * * *